United States Patent [19]

Rossignol

[11] Patent Number: 5,387,598
[45] Date of Patent: Feb. 7, 1995

[54] COMPOSITION AND GALENIC FORMULATION SUITABLE FOR COMBATTING AFFECTIONS OF THE LOWER ABDOMEN

[76] Inventor: Jean-François Rossignol, 2650 Heron La. S., Clearwater, Fla. 34622

[21] Appl. No.: 227,033

[22] Filed: Apr. 13, 1994

[51] Int. Cl.$^6$ .................. A61K 31/425; C07D 277/44
[52] U.S. Cl. ........................................ 514/371
[58] Field of Search ........................................ 514/371

[56] References Cited

U.S. PATENT DOCUMENTS

| | | | |
|---|---|---|---|
| 2,401,522 | 6/1946 | Stoll et al. | 260/306.8 |
| 2,735,798 | 2/1956 | Kupferbr et al. | 260/306.8 |
| 2,829,084 | 4/1958 | O'Neill et al. | 260/306.8 |
| 3,475,446 | 10/1969 | Capps | 260/306.8 |
| 3,950,351 | 4/1976 | Rossignol et al. | 260/306.8 |
| 4,315,018 | 2/1982 | Rossignol | 514/371 |

FOREIGN PATENT DOCUMENTS

| | | |
|---|---|---|
| 114277 | 8/1984 | European Pat. Off. |
| 2252730 | 8/1992 | United Kingdom |

OTHER PUBLICATIONS

Vignoles Ann. Rech. Vet. 22(4):359–363 1991, CA 118:207494g.
Murphy J. Appl. Toxicol. 5(2):49–52 (1985).
Rossignol Am. J. Trop. Med. Hyg. 33(3):511–512 May 1984.
Cavier Rev. Med. Vet. Toulouse 133(12):779–783 1982, CA 98:119237v.
Cavier Eur. J. Med. Chim-Chim. Ther. 13(6):539–543 (1978); CA 90:146304g.

*Primary Examiner*—Shep Rose
*Attorney, Agent, or Firm*—Sughrue, Mion, Zinn, Macpeak & Seas

[57] ABSTRACT

The present invention relates to a composition and a galenic formulation suitable for combatting affections of the lower abdomen, for example intestinal conditions such as diarrhea, said composition or formulation containing:

(a) an effective amount of a compound of formula I

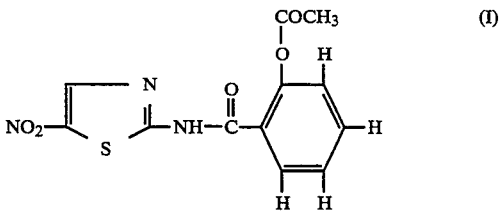

(b) at least one wetting agent, and preferably
(c) a starch derivative.

18 Claims, No Drawings

COMPOSITION AND GALENIC FORMULATION SUITABLE FOR COMBATTING AFFECTIONS OF THE LOWER ABDOMEN

THE STATE OF THE ART

Compositions for treating intestinal conditions or disorders are known.

For example EP 0114277 discloses compositions for expelling or destroying parasitic worms in the intestine. Said compositions in the form of an aqueous paste contain Febantel and Praziquantel as active agent, and Polysorbate 80 ® as wetting agent.

GB 2252730 teaches pharmaceutical compositions for the treatment of helminthiasis in warm-blooded animals. The compositions which are administered in a liquid form contain for example Praziquantel, benzimidazole, viscosity agents, surfactants, sanitizers, acidifiers and stabilizers.

All the said known compositions are not in a solid form, which render them difficult to be used.

Moreover, the efficiency of all said known compositions is limited.

It is also known that compound of formula I

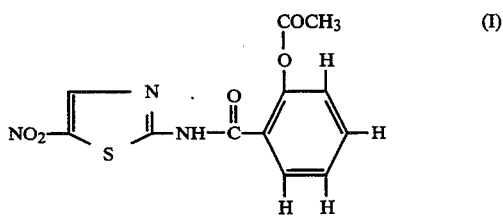

is effective against cestodes, nematodes and whipworms (U.S. Pat. No. 4,315,018) or is an interesting parasiticides, fungistatic and molluscicidal agent (U.S. Pat. No. 3,950,351).

The compound of formula I, which is also known as nitazoxanide or PH 5776 can be prepared by the method disclosed in U.S. Pat. No. 3,950,351, the content of which is incorporated hereby by reference in order to disclose a method for the manufacture of said compound.

Although some pharmaceutical compositions contain already a surfactant, it is unable to predict the efficiency of the active agent with or without surfactant. For many active agents, such as albendazole, the use of a surfactant has no influence on their efficiency.

Furthermore, wetting agents are considered as being agents causing some intestinal conditions or disorders.

It has now been disclosed that by using simultaneously a compound of formula I and a wetting agent, the efficiency of the compound was drastically increased and that by using such a mixture, it was possible to treat affections of the lower abdomen, such as intestinal conditions (diarrhea), gastrointestinal infections, enteric infections, sexually transmitted infections, vaginal infections and urinogenetical infections.

In view of its excellent efficiency, possible secondary effects of the compound of formula (I) could be avoided or prevented.

BRIEF DESCRIPTION OF THE INVENTION

The present invention relates to a composition, preferably a solid composition, for oral administration for combatting affections or infections of the lower abdomen, preferably intestinal and vaginal conditions, said composition containing:

an effective amount of an active agent of formula I

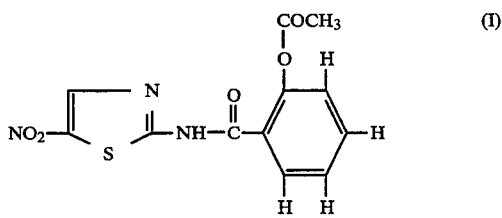

a wetting agent, and preferably
at least one starch derivative.

The composition may also contain other active agents, for example an anthimintic agent such as febantel, praziquantel, levamisole, albendazole, oxfendazole, moxidectin, ivermectin, milbemycins, etc.

The preparation and use of compound of formula I is disclosed in U.S. Pat. No. 3,950,351 and U.S. Pat. No. 4,315,018.

The wetting agent present in the composition of the invention is advantageously an anionic surfactant, and is preferably selected among the group consisting of sugar esters, polyoxyethylene, polyoxypropylene, anhydrohexitol derivatives, fatty alkanol amides, fatty amine oxides, sucrose, mannitol, sorbitol, lecithins, polyvinylpyrrolidones, fatty acid esters, glycerides of sucrose, esters of xylose, polyoxyethylene glycerides, esters of fatty acids and polyoxyethylene ether of fatty alcohols and polyoxyethylene fatty acid esters of sorbitan, polyoxyethyelene esters of fatty acids of sorbitan, glyceridepolyglycides esters of alcohol polyglycides and mixture thereof.

Particularly suitable wetting agents are saccharose distearate, PVP (polyvinylpyrrolidone), etc.

The composition according to the invention contains preferably a starch derivative, especially a carboxy derivative of starch such as carboxymethyl starch, and natrium derivative thereof or a salt thereof.

The composition contains, for example, up to 20% by weight, advantageously 1 to 10% by weight of surfactant with respect to the weight of active agent(s), and up to 20% by weight, advantageously 1 to 10% by weight of starch derivative with respect to the weight of active agent(s).

The invention relates also to a galenic formulation for oral administration for combatting affections of the lower abdomen, such as intestinal, vaginal or urogenital conditions or disorders, said galenic formulation comprising a core containing a composition containing:

an effective amount of an active agent of formula I;
a wetting agent, and
a starch derivative or a salt thereof
the water content of said composition being less than 25% by weight, the said core being preferably coated with a membrane. Such a membrane can be a membrane insoluble in the acid gastric medium, but soluble in the intestine.

The preferred compositions, wetting agents, etc of the galenic formulation are those disclosed hereabove for the composition according to the invention.

The invention relates yet to the use of the composition or the galenic formulation for the treatment of diarrhea.

The invention relates also to an ointment or gel for the treatment of organs of the lower abdomen, such as vaginal or urogenital conditions or disorders, disorders of the rectum. The ointment, preferably in the gel form, comprises an active agent of formula (I), a wetting agent as well as excipient.

The wetting agent is preferably one of those listed above for the composition and/or galenic formulation.

Furthermore, the invention relates to an antibacterial composition containing a compound of formula I and a wetting agent. Such a composition is active against aerobic as well anaerobic bacteria, the composition having thus a very large spectra of activity.

The invention relates thus also to a process for killing bacteria or for preventing the presence or growth of bacteria in a medium. In said process, the bacteria or medium is treated with a bactericidal composition according to the invention, for example by spraying the composition on the bacteria, by immersing a support into a medium, etc.

The invention relates also to a process for treating diarrhea affections of animals, preferably humans, in which a composition containing:

an effective amount of an active agent (I)

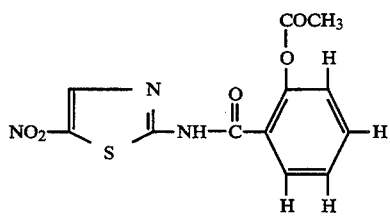

a wetting agent
a starch derivative is orally administered.

The invention relates furthermore to a food composition such as a food pasta or a yaourt comprising, as preserving agent, an effective amount of an active agent (I);

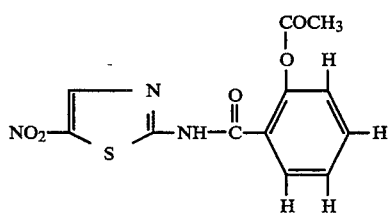

a wetting agent, and
a starch derivative

DESCRIPTION OF EXAMPLES OF COMPOSITIONS AND GALENIC formulations according to the invention.

2-(2'-Acetoxy)-benzamido-5-nitro-thiazole (i.e. a compound of formula I) has been used for the preparation of said compositions and galenic formulations.

Said compound is also known under the name nitazoxanide (PH 5776).

Said compound has the form of a light yellow powder and is not water soluble.

Composition A 100 g nitazoxanide was mixed in 100 ml water with 10 g of polyvinylpyrrolidone (wetting agent) and 5 g carboxymethyl starch. The mixture has been dried under vaccum.

Said composition can then be used for making granules, sachets, tablets or capsule for buccal or oral administration.

Compositions B,C,D,E,F,G

Compositions similar to composition A were prepared, except that only 5 g and 2 g of polyvinylpyrrolydone, and 2 g and 1 g carboxymethyl starch were used.

The following table gives the content (g) of nitazoxanide "N", polyvinylpyrrolidone "PVP" and carboxymethyl starch "CS" of the compositions.

| Composition | N (g) | PVP (g) | CS (g) |
|---|---|---|---|
| C | 100 | 5 | 5 |
| D | 100 | 2 | 2 |
| E | 100 | 5 | 2 |
| F | 100 | 5 | 1 |
| G | 100 | 5 | 0 |

Compositions H, I, J

Compositions containing nitazoxanide, as well as another active agent have been prepared by preparing an aqueous medium containing PVP and carboxymethyl starch and by adding to said medium nitazoxanide and another active agent. The medium was then dried to obtain a water content lower to 5%.

| Composition | N g | PVP g | CS g | Other active agent g | Water content % |
|---|---|---|---|---|---|
| H | 50 | 5 | 2 | Praziquantel 50 | 2 |
| J | 75 | 5 | 2 | Praziquantel 50 | 1 |
| I | 75 | 5 | 2 | Praziquantel 50 | 2 |

Galenic formulation 500 g Nitazoxanide in powder has been mixed with 10 g polyvinylpyrrolidone, 20 g carboxymethyl starch, 25 g corn starch, 5 g magnesium stearate and 50 g water, and the so obtained mixture was then formed into granules of 560 mg (i.e. granules containing 500 mg of active agent). The granules which had a diameter of about 1 cm were then dried at about 50° C.

The so obtained microgranules were then provided with a coating obtained by spraying a hot sugar solution. The sugar coating formed a membrane.

It is obvious that the microgranules may also contain one or several excipients or other active agents, such as microcristalline cellulose (Avicel ® FMC), methylcellulose, ethylcellulose, carboxymethylcellulose, hydroxyethylcellulose, hydroxypropylcellulose, starch, etc.

In the same way, the membrane may also comprise:
a pharmacological acceptable excipient such as a plastifiant, a pigment, a filler, a wetting agent, a lubricant, ... or a mixture thereof, and
a film forming composition which comprises a substance insoluble in the gastric acid but entero soluble (polymeric substance or not, for example cellulose acethophthalate, polyvinyle acetophthalate, hydroxypropylmethylcellulose, ...).

The compositions and galenic forms according to the invention can be used for the treatment of animals and humans suffering of intestinal troubles, such as diarrhea, vaginal affections, urogenital affections.

It has also been observed that by using compositions or galenic forms according to the invention, it was possible to have a reduction or suppression of parasites in the feces such as Cryptosporidium parvum, Enterocytozoon bieneusi, Giardia intestinalis, isospora belli, etc; of ascariasis (roundworms), of ancylostomiasis (whipworms), . . .

TEST 1

In order to show the effectiveness of the composition according to the invention, two groups of 5 mices (4–8 weeks old; 18–20 g weight) each were tested, one group being infected with Cryptosporidium parvum, wgile the other group was not infected.

The infected mices suffered of chronic diarrhea.

Before the treatment, it was easy to determine the mices suffering of chronic diarrhea.

The treatment takes place by using the composition D of nitazoxanide disclosed hereinbefore. The mices suffering of chronic diarrhea received by oral gavage during one week, each day about 0.01 g of nitazoxanide (i.e. about 0.6 g/kg mice).

After one week of treatment, it was no more possible to determine by fecal analysis which group of mices suffered firstly of diarrhea.

Test II

Aqueous compositions (100 g) containing 10 g of an active agent have been prepared.

For the composition containing nitazoxonide as active agent, the composition contained furthermore 0.5 g saccharose distereate.

Said compositions have been used for treating various parasites, helminths, bacteria and fungus.

The activity of the compositions is given in the following table:

| | ACTIVITY OF | | | |
|---|---|---|---|---|
| | Nitazo-xanide + sac-charose distear-ate | Albenda-zole | Mebenda-zole | Metron-idazole |
| Protozoa | | | | |
| Trichomonas vaginalis | + | No | No | + |
| Trichomonas intestinalis | + | No | No | + |
| Entamoeba histolytica | + | No | No | + |
| Entamoeba dispar | + | No | No | + |
| Entamoeba coli | + | No | No | + |
| Endolimax nana | + | No | No | + |
| Balantidium coli | + | No | No | + |
| Dientamoeba fragilis | + | No | No | + |
| Giarda lamblia | + | No | No | + |
| Isospora belli | + | +/− | No | + |
| Cryptosporidium parvum | + | No | No | No |
| Bladtocystis hominis | + | No | No | No |
| Enterocytozoon bieneusi | + | No | No | No |
| Septata intestinalis | + | No | No | No |
| Helminths | | | | |
| Enterobius vermicularis | + | + | + | No |
| Ascaris lumbricoides | + | + | + | No |

| | ACTIVITY OF | | | |
|---|---|---|---|---|
| | Nitazo-xanide + sac-charose distear-ate | Albenda-zole | Mebenda-zole | Metron-idazole |
| Necator americanus | + | + | + | No |
| Anycylosloma duodenale | + | + | + | No |
| Trichuris trichiura | + | + | + | No |
| Strongyloides stercoralis | + | No | No | No |
| Taenia saginata | + | No | No | No |
| Taenia solium | + | No | No | No |
| Hymenolepis nana | + | No | No | No |
| Bacteria aerobic | | | | |
| Staphylococcus aureus | + | No | No | No |
| Escherichia coli | + | No | No | No |
| Protens vulgaris | + | No | No | No |
| Bacteria anaerobic | | | | |
| Clostridum species | + | No | No | + |
| Bacteroides species | + | No | No | + |
| Peptococcus species | + | No | No | + |
| Peptostreptococcus SPP | + | No | No | + |
| Fusobacterium SPP | + | No | No | + |
| Fungus | | | | |
| Candida Albicans | + | No | No | No |
| Trychophyton Mentagrophytes | + | + | No | No |
| Microsporum audovini | + | + | No | No |
| Epidermophyton flocosum | + | + | No | No |

What i claim is:

1. Composition for oral administration for combatting affections of the lower abdomen, said composition containing:

an effective amount of an active agent of formula I

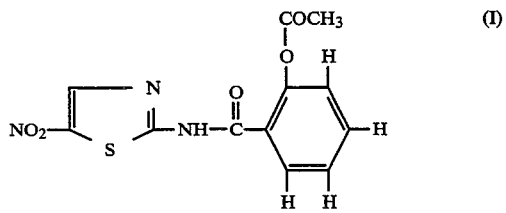

and a wetting agent.

2. The composition of claim 1, in which at least one wetting agent is selected among the group consisting of the anionic surfactants.

3. The composition of claim 1, in which the wetting agent is selected from the group consisting of sugar esters, polyoxyethylene, polyoxypropylene, anhydrohexitol derivatives, fatty alkanol amides, fatty amine oxides, sucrose, mannitol, sorbitol, lecithins, polyvinylpyrrolidones, fatty acid esters, glycerides of sucrose, esters of xylose, polyoxyethylene glycerides, esters of fatty acids and polyoxyethylene ether of fatty alcohols and polyoxyethylene fatty acids esters of sorbitan, polyoxyethylene esters of fatty acids of sorbitan, glyceride-polyglycide esters of alcohol polyglycides and mixtures thereof.

4. The composition of claim 1, which contains a starch derivative.

5. The composition of claim 1, which contains carboxymethyl starch or a salt thereof.

6. The composition of claim 1, which contains up to 20% by weight of surfactant with respect to the weight of active agent and up to 20% by weight of starch derivative with respect to the weight of active agent.

7. Galenic formulation for oral administration for combatting affections of the lower abdomen, said galenic form comprising a core containing a composition containing:

an effective amount of an active agent of formula I

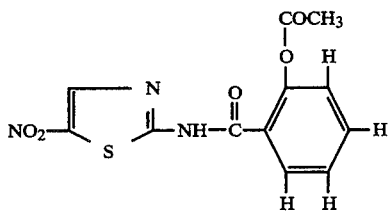

wetting agent, and
a starch derivative,
the water content of said composition being less than 25% by weight.

8. The formulation of claim 7, containing carboxymethyl starch or a salt thereof.

9. Ointment for the treatment for combatting affections of the lower abdomen, containing:

an effective amount of active agent of formula (I)

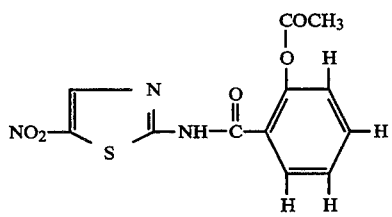

and
a wetting agent.

10. The ointment of claim 9, which contains a starch derivative.

11. The ointment of claim 8, in which the wetting agent is selected from the group consisting of sugar esters, polyoxyethylene, polyoxypropylene, anhydrohexitol derivatives, fatty alkanol amides, fatty amine oxides, sucrose, mannitol, sorbitol, lecithins, polyvinylpyrrolidones, fatty acid esters, glycerides of sucrose, esters of xylose, polyoxyethylene glycerides, esters of fatty acids and polyoxyethylene ether of fatty alcohols and polyoxyethylene fatty acids esters of sorbitan, polyoxyethylene esters of fatty acids of sorbitan, glyceride-polyglycide esters of alcohol polyglycides and mixtures thereof.

12. The ointment of claim 9, which contains carboxymethyl starch.

13. Bactericidal composition containing as bactericidal agent, a mixture of an active agent of formula (I)

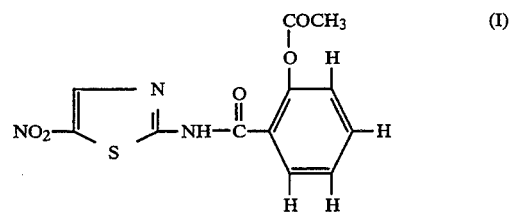

and a wetting agent.

14. The bactericidal composition of claim 2, in which the wetting agent is selected from the group consisting of sugar esters, polyoxyethylene, polyoxypropylene, anhydrohexitol derivatives, fatty alkanol amides, fatty amine oxides, sucrose, mannitol, sorbitol, lecithins, polyvinylpyrrolidones, fatty acid esters, glycerides of sucrose, esters of xylose, polyoxyethylene glycerides, esters of fatty acids and polyoxyethylene ether of fatty alcohols and polyoxyethylene fatty acids esters of sorbitan, polyoxyethylene esters of fatty acids of sorbitan, glyceride-polyglycide esters of alcohol polyglycides and mixtures thereof.

15. Process for combatting aerobic and anaerobic bacteria in which the bacteria are treated with a bactericidal composition containing as bactericidal agent, a mixture of an active agent of formula (I), and a wetting agent

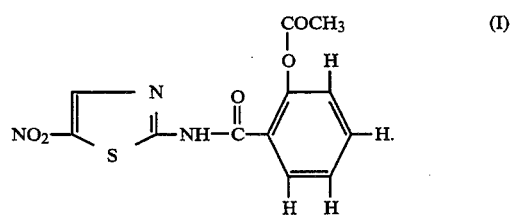

16. Process for preventing the growth of bacteria into a medium, in which the medium is treated with a bactericidal composition containing as bactericidal agent, a mixture of an active agent of formula (I), and a wetting agent

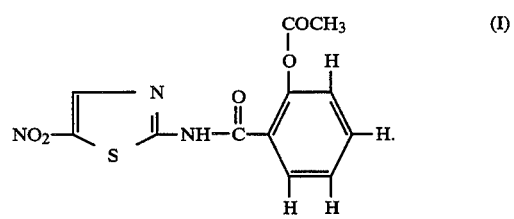

17. Process for treating diarrhea affections of animals, in which a composition containing:

an effective amount of an active agent (I)

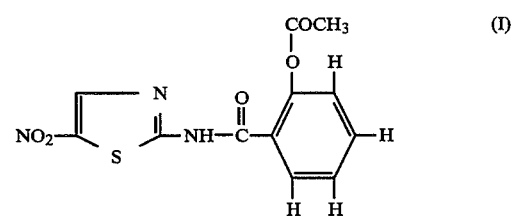

a wetting agent, and a starch derivative is orally administered.
18. Food composition comprising, as preserving agent,
an effective amount of an active agent (I)
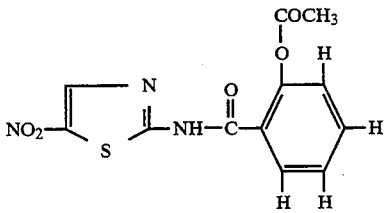
a wetting agent, and
a starch derivative.
* * * * *